(12) United States Patent
Weese et al.

(10) Patent No.: US 11,383,103 B2
(45) Date of Patent: Jul. 12, 2022

(54) EVALUATION OF AN ANATOMIC STRUCTURE WITH RESPECT TO A DOSE DISTRIBUTION IN RADIATION THERAPY PLANNING

(71) Applicant: KONINKLIJKE PHILIPS N.V., Eindhoven (NL)

(72) Inventors: Rolf Jürgen Weese, Nortderstedt (DE); Steffen Renisch, Hamburg (DE); Hrishikesh Narayanrao Deshpande, Hamburg (DE); Heinrich Schulz, Hamburg (DE); Sven Kabus, Hamburg (DE); Stéphane Allaire, Nanterre (FR); Alfonso Agatino Isola, Eindhoven (NL); Christoph Neukirchen, Aachen (DE); Maria Luiza Bondar, Waalre (NL); Jens Wiegert, Aachen (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 203 days.

(21) Appl. No.: 16/770,676

(22) PCT Filed: Dec. 17, 2018

(86) PCT No.: PCT/EP2018/085098
§ 371 (c)(1),
(2) Date: Jun. 8, 2020

(87) PCT Pub. No.: WO2019/121436
PCT Pub. Date: Jun. 27, 2019

(65) Prior Publication Data
US 2021/0162234 A1 Jun. 3, 2021

(30) Foreign Application Priority Data
Dec. 18, 2017 (EP) .................................. 17306794

(51) Int. Cl.
*A61N 5/10* (2006.01)
(52) U.S. Cl.
CPC ......... *A61N 5/1038* (2013.01); *A61N 5/1031* (2013.01); *A61N 5/1039* (2013.01)
(58) Field of Classification Search
None
See application file for complete search history.

(56) References Cited

U.S. PATENT DOCUMENTS

| 11,135,448 B2 * | 10/2021 | Morgas | ................ A61N 5/1038 |
| 2005/0111621 A1 * | 5/2005 | Riker | ..................... G16H 70/20 378/65 |

(Continued)

FOREIGN PATENT DOCUMENTS

| EP | 2878338 A1 | 6/2015 |
| WO | 2013030707 A1 | 3/2013 |
| WO | 2017044562 A1 | 3/2017 |

OTHER PUBLICATIONS

International Search Report and Written Opinion for PCT/EP2018/085098, dated Apr. 1, 2019.

(Continued)

*Primary Examiner* — Hoon K Song

(57) ABSTRACT

The invention relates to a system for assisting in evaluating a contour of an anatomic structure (22) with respect to a dose distribution corresponding to a treatment plan for a radiation therapy treatment of a patient. The system comprises an evaluation unit particularly configured to evaluate the dose distribution in varying distances from the contour of the anatomic structure (22) to determine at least one point where the evaluated dose distribution fulfills a predetermined condition, and to determine the distance between the at least one point and the contour and/or to visualize the at least one point to a user of the system.

15 Claims, 2 Drawing Sheets

(56) References Cited

U.S. PATENT DOCUMENTS

| | | | |
|---|---|---|---|
| 2008/0002811 A1 | 1/2008 | Allison | |
| 2009/0187422 A1 | 7/2009 | Kaus | |
| 2010/0183121 A1 | 7/2010 | Riker | |
| 2012/0280135 A1 | 11/2012 | Bal | |
| 2012/0326057 A1* | 12/2012 | Remeijer | A61N 5/1031 250/492.1 |
| 2015/0087879 A1* | 3/2015 | Nelms | A61N 5/103 600/1 |
| 2015/0209600 A1 | 7/2015 | Overweg | |
| 2015/0297916 A1 | 10/2015 | Chen | |
| 2017/0095678 A1* | 4/2017 | Oster | A61N 5/1067 |
| 2019/0076671 A1* | 3/2019 | Willcut | A61N 5/1039 |
| 2021/0201475 A1* | 7/2021 | Bose | G06T 7/11 |

OTHER PUBLICATIONS

Thornqvist, Sara et al, "Propagation of Target and Organ at Risk Contours in Radiotherapy of Prostate Cancer using Deformable Image Registration", Acta Oncologica, vol. 49, No. 7, 2010, pp. 1023-1032.

Veiga, Catarina et al Toward Adaptive Radiotherapy for Head and Neck Patients: Feasibility Study on using CT-to-CBCT Deformable Registration for "Dose of the Day" Calculations. Mecial Physics, vol. 41, No. 3, 2014.

Hahn, P. et al "Colour Visualization as an Aid to the Comparision of Treatment Plans for Prostatic Carcinoma", Acta Oncologica, vol. 26, 1987.

* cited by examiner

EVALUATION OF AN ANATOMIC STRUCTURE WITH RESPECT TO A DOSE DISTRIBUTION IN RADIATION THERAPY PLANNING

CROSS-REFERENCE TO PRIOR APPLICATIONS

This application is the U.S. National Phase application under 35 U.S.C. § 371 of International Application No. PCT/EP2018/085098, filed on Dec. 17, 2018, which claims the benefit of European Patent Application No. 17306794.3, filed on Dec. 18, 2017. These applications are hereby incorporated by reference herein.

FIELD OF THE INVENTION

The invention generally relates to the planning of a radiation therapy treatment. More specifically, the invention relates to a system and a method for assisting in evaluating a contour of an anatomic structure with respect to a dose distribution corresponding to a treatment plan for a radiation therapy treatment of a patient. Moreover, the invention relates to a computer program for carrying out the method.

BACKGROUND OF THE INVENTION

In radiation therapy, target structures, such as tumors, within patients' bodies are treated by means radioactive or electromagnetic radiation or ultrasound waves in order to control growth of or kill cancer cells. At the same time, the treatment is delivered in such a way that the radiation or thermal dose delivered to surrounding healthy structures, which are usually also referred to as organs at risk (OARs), is as low as possible.

The treatment parameters for controlling a radiation therapy treatment are defined in a treatment plan, which is generated in a planning procedure on the basis of treatment goals specifying requirements for the radiation dose or thermal dose delivered to target structure. In the planning procedure, an optimization process is carried out using a planning image of the region of the patient body including the target structure and the surrounding OARs to find the treatment plan which results in an optimized radiation dose distribution that fulfills the treatment goals.

In this planning procedure, the treatment plan is generated on the basis of the positions and contours of the target structure and the OARs as determined in the planning image. However, these positions and contours may change during the treatment and even prior to the treatment, if there is a greater time interval between the time of the acquisition of the planning image and the beginning of the treatment. In order to take account of such changes, one or more further images may be acquired to determine the changed positions and shapes of the target structure and/or the OARs and the treatment plan may be adapted to the these changed positions and shapes, if necessary. However, also these positions and shapes of the target structure and the OARs as determined on the basis of the further image(s) may deviate from the actual positions and shapes of the target structure and the OARs during the treatment.

One reason for such inaccuracies of the analyzed positions and shapes of the target structure and the OARs as determined on the basis of the further image(s) with respect to their actual positions and shapes during the treatment may be deformations of the patient's anatomy, e.g. caused by the positioning of the patient during the treatment which deviates from the positioning for acquiring the further image(s) or the response of the patient's anatomy to the treatment.

Moreover, the positions and contours of the target structure and the OARs in the further image(s) are often determined on the basis of deformable image registration (DIR) using the contours determined in the planning image. In this process, an elastic transformation may be determined to map the planning image and the further image(s) (or vice versa). This transformation (or its inverse) may then be applied to the contours of the target structure and the OARs in the planning image in order to determine the changed position and contours of the target structure and the OARs. However, the transformed contours and their positions usually include a certain error resulting from inaccuracies of the DIR.

The aforementioned inaccuracies of the analyzed positions and shapes of the target structure and/or the OARs with respect to their actual positions and shapes during the treatment limit the accuracy of assessments of a dose distribution with respect to the changed positions and contours of the target structure and the OARs and may prevent an appropriate re-planning of the treatment. In particular, this assessment may include an estimation of a dose absorbed by the target structure and the OARs and the aforementioned inaccuracies limit the accuracy of these estimates.

In this respect, it would be desirable to evaluate the impact of inaccuracies of the contour of the relevant anatomic structures on the evaluation of a dose distribution with respect to this contour.

SUMMARY OF THE INVENTION

It is therefore an object of the present invention to allow for estimating an impact of inaccuracies of a determined contour of an anatomic structure with respect to the actual contour during a radiation therapy treatment on an evaluation of a dose distribution with respect to this contour.

In one aspect, the invention suggests a system for assisting in evaluating a contour of an anatomic structure with respect to a dose distribution corresponding to a treatment plan for a radiation therapy treatment of a patient. The system comprises an evaluation unit configured to
- receive the contour of the anatomic structure and the dose distribution,
- evaluate the dose distribution in varying distances from the contour of the anatomic structure to determine at least one point where the evaluated dose distribution fulfills a predetermined condition, and
- determine the distance between the at least one point and the contour and/or to visualize the at least one point to a user of the system.

Since the evaluation unit is configured to determine at least one point where the evaluated dose distribution fulfills a predetermined condition by evaluating the dose distribution in varying distances to the contour of the anatomic structure, the influence of an error of the contour on an evaluation of the dose distribution on the basis of the contour can be assessed, particularly on the accuracy of this evaluation. In particular, it is possible to assess the influence of an error of the contour on an estimate of the dose absorbed by the anatomic structure and/or on a conformance with a dose requirement for the anatomic structure as determined on the basis of the dose distribution and the contour.

The influence of an error of the contour of the anatomic structure on the evaluation of the dose distribution may be higher, if the determined at least one point is closer to the contour. Therefore, the distance between the at least one point and the contour may be determined by the evaluation unit. In addition or as an alternative, the evaluation unit may visualize the at least one point. This particularly allows the user of the system to estimate the distance between the at least one point and the contour and, thus, to assess an influence of an error of the contour on the dose evaluation.

In one embodiment of the invention, the evaluation unit is configured to determine the at least one point by evaluating the dose distribution along at least one path extending from the contour of the anatomic structure in an inward or outward direction, the at least one point lying on the path. In a related embodiment, the path corresponds to a ray being arranged essentially perpendicular to the contour of the anatomic structure.

In these embodiments, the determined at least one point can particularly be related to a position on the contour. This position may particularly correspond to the intersection point of the path and the contour. At this point and in the vicinity thereof, smaller errors of the contour may have a larger influence on the evaluation of the dose distribution, if the point is closer to the contour of the anatomic structure.

In one embodiment of the invention, the predetermined condition and/or the direction of the path is selected on the basis of a type of the anatomic structure and/or on the basis of the dose goal to be achieved for the anatomic structure in the radiation therapy treatment. With respect to the type of the anatomic structure, the evaluation unit may particularly distinguish between target structures of the radiation therapy treatment and OARs.

The predetermined condition may be fulfilled if the dose distribution has a predetermined characteristic value. In one embodiment of the invention, the characteristic value corresponds to a predetermined maximum dose value or a predetermined minimum dose value. In a related embodiment of the invention, the maximum dose value corresponds to a maximum dose or a maximum average dose to be delivered to the anatomic structure during the treatment or to a dose value exceeding the maximum dose or the maximum average dose by a predetermined amount. In a further related embodiment of the invention, the minimum dose value corresponds to a minimum dose or a minimum average dose to be delivered to the anatomic structure during the treatment or to a dose value lower than the minimum dose or the minimum average dose by a predetermined amount.

In a further embodiment of the invention, the predetermined condition is fulfilled if the dose distribution has a predetermined characteristic value in a region surrounding the at least one point. This embodiment particularly takes account of situations in which the dose distribution exhibits greater dose variations in the vicinity of the point so that deviations of the assessed contour from the actual contour may have a greater influence on the evaluation of the dose distribution also in case the dose distribution has a predetermined characteristic (only) in the vicinity of the path.

In one embodiment of the invention, the predetermined condition relates to a dose goal to be achieved by the anatomic structure in the radiation therapy treatment and the evaluation unit is configured to visualize information indicative of the influence of an error of at least part of the contour on a conformance with the dose goal as determined on the basis of the dose distribution and the contour, the information being derived from the at least one point and/or from the determined distance between the at least one point and the contour.

In one implementation, the information may comprise a visualization of the determined at least one point. This visualization allows the user of the system to determine the distance between the at least one point and the contour (which does not have to be determined automatically in this implementation) and to assess an influence of an error of the at least part of the contour on the conformance with the dose goal, as determined on the basis of the dose distribution and the contour, by inspecting the visualization.

Further, one embodiment of the invention includes that the evaluation unit is configured to determine plural points where the evaluated dose distribution fulfills the predetermined condition and to display a sensitivity region, which is bounded by the contour of the anatomic structure and the plural points, to the user of the system. This embodiment allows for visualizing a sensitivity region around the anatomic structure, which allows the user to easily assess the influence of errors of the contour on the evaluation of the dose distribution and to determine critical sections of the contour, where the distance between the section and boundary of the sensitivity region is small.

As said above, the influence of an error of at least part of the contour on the evaluation of the dose distribution may be higher, if the determined at least one point is closer to the contour. Particularly in view of this one embodiment of the invention includes that the evaluation unit is configured to compare the distance between the at least one point and the segmented contour of the anatomic structure with a predetermined threshold. The threshold may particularly serve to identify points or sections of the contour, where the accuracy of the contour has a high influence on the evaluation of the dose distribution.

The contour of the anatomic structure may be generated by transforming a further contour of the anatomic structure using a transformation determined by means of a deformable image registration between the image and a further image showing the anatomic structure. In this case, the predetermined threshold may be derived on the basis of an inaccuracy of the deformable image registration. Moreover, inaccuracies of the contour may result from potential deformations of the patient anatomy. In this respect, the predetermined threshold may be determined on the basis of an expected amount of such deformations.

In one embodiment of the invention, the evaluation unit is configured to display a visualization highlighting an origin of the path on the contour of the anatomic structure, if the distance between the at least one point on the at least one path and the contour of the anatomic structure is smaller than the predetermined threshold. Hereby, the user can easily identify potentially critical points of the contour, where errors of the contour have a higher influence on the evaluation of the dose distribution. The highlighting may particularly be achieved by coloring the relevant point of the contour using a predetermined color.

In a further variant, each of a plurality of distance intervals is assigned to a visual code and the evaluation unit is configured to display an origin of the at least one path on the contour in accordance with the visual code assigned to the distance interval including the distance between the at least one point and the contour of the anatomic structure. In this embodiment, the user is not only provided with highlighting information for determining a point having a distance to the contour of the anatomic structure, which exceeds the threshold. Rather, the user can also determine the distance on the basis of the visual code in order to more accurately assess the influence of an error of the contour at the at least one point on the evaluation of the dose distribution on the basis of the contour. The visual code used in this embodiment may correspond to a color code.

In a further aspect, the invention suggests a method for assisting in evaluating a contour of an anatomic structure with respect to a dose distribution corresponding to a treatment plan for a radiation therapy treatment of a patient. The method comprises the steps of:

receiving the segmented contour of the anatomic structure and the dose distribution, evaluating the dose distribution in varying distances from the contour of the anatomic structure to determine at least one point where the evaluated dose distribution fulfills a predetermined condition relating, and determining the distance between the at least one point and the contour and/or visualizing the at least one point to a user of the system.

In a further aspect, the invention suggests a computer program comprising program code for instructing a computer device to perform the method when the program code is executed in the computer device.

It shall be understood that the system of claim 1, the method of claim 14 and the computer program of claim 15, have similar and/or identical preferred embodiments, in particular, as defined in the dependent claims.

It shall be understood that a preferred embodiment of the present invention can also be any combination of the dependent claims or above embodiments with the respective independent claim.

These and other aspects of the invention will be apparent from and elucidated with reference to the embodiments described hereinafter.

DETAILED DESCRIPTION OF EMBODIMENTS

Figure 1:
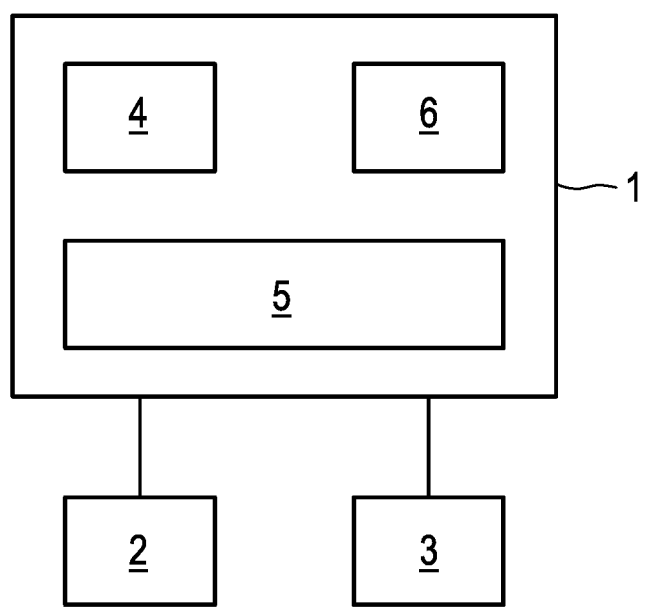
FIG. 1 schematically and exemplarily illustrates components of a planning system for planning an adaptive radiation therapy treatment of a patient, and FIG. 2 schematically and exemplarily illustrates rays extending from a surface of an anatomic structure and a dose distribution which is evaluated along the rays, and FIG. 3 schematically and exemplarily illustrates steps of a method for estimating an influence of an error of a contour of an anatomic structure to an accuracy of an evaluation of a dose distribution.

FIG. 1 schematically and exemplarily shows components of a planning system for planning an adaptive radiation therapy treatment of a patient. The radiation therapy treatment may be carried out using radioactive radiation generated by radiation source implanted into the patient body as it is the case in brachytherapy, for example, or it may be configured as an external beam radiation therapy treatment, where the treatment is carried out using ionizing radiation that is delivered to the patient body from the outside thereof. In further embodiments, the radiation therapy treatment may be configured as an electromagnetic therapy treatment using non-ionizing electromagnetic radiation or a high-intensity focused ultrasound (HIFU) treatment.

During the treatment a prescribed accumulated radiation dose or thermal dose is delivered to a target structure within the patient body, which may particularly by a tumor, in order to kill or control growths of cancer cells. For this purpose, the treatment may be delivered in one fraction or in several separate fractions, which have a certain time distance between them.

The treatment may be delivered on the basis of a treatment plan, which specifies the relevant treatment parameters for controlling the operation of the treatment equipment such that a planned radiation or thermal dose is delivered to the target structure and the surrounding region of the patient body during the treatment. The treatment plan is generated in the planning system of FIG. 1 in a user-assisted procedure.

The planning system may be implemented in a computer device 1, such as, for example a personal computer, comprising a processing unit which executes a treatment planning software. Further, the planning system comprises a suitable interface for receiving images of the patient as will be explained herein below. Moreover, the planning system comprises or is coupled to a user interface for interacting with a user (which may e.g. be a physician). The user interface may particularly comprise a display unit 2 and an input device 3. The input device 3 may allow for navigating within a graphical user interface provided on the display unit 2. For this purpose, the input device 3 may particularly comprise a pointing device, such as, for example, a computer mouse, a track pad or a trackball. Likewise, the display unit 2 may comprise a touch-sensitive monitor which also serves as input device 3.

In order to generate the treatment plan, the planning system may comprise a planning unit 4. In the planning unit 4, the treatment plan may be generated such that a prescribed radiation or thermal dose is delivered to the target structure and that the radiation or thermal dose delivered to the surrounding OARs is kept below predetermined limits. However, in the following only the term "dose" is used in this respect and it is to be understood that this term refers to a radiation dose or a thermal dose depending on the applied radiation therapy modality.

More specifically, the treatment plan may be generated on the basis of an image of the region of interest of the patient body including the target structure and the surrounding OARs. This image is also referred to as planning image herein. The planning image may be acquired in accordance with a suitable imaging modality, such as, for example computed tomography (CT) imaging. In the planning image the target structure and the relevant OARs may be segmented using an automatic, semi-automatic or manual segmentation method as known to a person skilled in the art in order to determine the positions and contours of the target structure and the OARs.

Further, the treatment plan may be generated on the basis of a clinical prescription for the patient, which may particularly specify treatment goals with respect to the target structure. These treatment goals may include the delivery of a certain minimum dose to the target structure during the treatment. In addition, treatment goals with respect to the OARs may be specified. These treatment goals may include the delivery of maximum doses to be delivered to the OARs.

On the basis of the treatment goals and the planning image including the segmented contours of the target structure and the OARs, the planning unit 4 generates the treatment plan to achieve an optimized radiation dose distribution during the treatment such that the treatment goals are fulfilled. In order to generate the treatment plan in such a way, the planning unit 4 carries out an optimization procedure to determine optimized values of relevant treatment parameters. In the optimization procedure, a cost function including the treatment parameters may be set up on the basis of the treatment goals in a way known to the person skilled in the art and minimized with respect to the treatment parameters. This may be done using an automatic minimization algorithm and/or in a user-guided iterative optimization procedure comprising several steps.

In each step of the user-guided iterative optimization procedure, the planning unit 4 automatically calculates a preliminary treatment plan by approximating a solution of the optimization problem. Then, the planning unit 4 determines the dose distribution corresponding to this treatment plan and visualizes the dose distribution to the user of the planning unit 4. The user then reviews the dose distribution to decide whether he/she is satisfied with the dose distribution. If this is the case in one step, the treatment plan calculated in this step is used as the pre-optimized treatment plan. If the user is not satisfied, the optimization problem is modified in accordance with changes specified by the user as a result of his/her review. Then, the planning unit 4 calculates a new preliminary treatment plan in the next step and the procedure continues until an acceptable dose distribution is achieved.

In such a way, the planning unit 4 may determine an optimized treatment plan and a corresponding optimized dose distribution, which may be estimated in the planning unit 4 on the basis of the treatment means used for delivering the treatment. This optimized treatment plan is generated in view of the positions and segmented contours of the target structure and the OARs as included in the planning image. However, these positions and contours may change during the treatment due to intra-fraction motion and/or due to inter-fraction motion of the target structure and/or the OARs. Moreover, if there is a greater time interval between the time of the acquisition of the planning image and the beginning of the treatment, the actual position and contour of the target structure and/or the OARs may significantly deviate from their positions and contours shown in the planning image.

Therefore, the treatment plan may be adapted to the changed position and shape of the target structure and/or the OARs once or several times during the treatment or immediately before the beginning of the treatment in a plan adaptation unit 6 of the planning system. Each plan adaptation may be carried out in the basis of a new image of the region of interest of the patient body acquired immediately before the beginning of the treatment or during the treatment.

In this image, the target structure and the OARs may again be segmented using a suitable segmentation procedure in order to determine their (changed) contours and positions. As an alternative, the positions and contours of the target structure and the OARs in the further image may be determined on the basis of DIR using the contours determined in a reference image, which may particularly correspond to the planning image. In this process, an elastic transformation may be determined in a way known to the person skilled in the art to transform the reference image such that it corresponds to the new image (or vice versa). This transformation (or its inverse) may then be applied to the segmented contours of the target structure and the OARs in the reference image in order to determine the changed position and contours of the target structure and the OARs. In such a way, these changed positions and contours can be determined quickly and efficiently.

Upon having determined the changed positions and contours of the target structure and the OARs included in the new image, it may be evaluated whether the optimized dose distribution corresponding to the initial or previously used treatment plan still allows for satisfying the treatment goals. If this is not the case, a re-planning process may be performed and in this process a new optimized dose treatment plan by adapting the initial treatment plan on the basis of the changed positions and contours of the target structure and the OARs.

In this process, dose distributions have to be evaluated with respect to the changed positions and contours of the relevant anatomic structures as determined on the basis of the new image of the patient anatomy. In particular, a corresponding evaluation has to be performed for the dose distribution corresponding to the initial or previously used treatment plan. In addition, such an evaluation may have to be performed for the adapted dose distribution corresponding to the revised treatment plan as determined in the plan adaptation unit in order to validate this dose distribution in view of the treatment goals.

However, the determined contours and their positions usually include a certain error with respect to the actual contours and positions of the target structure and the OARs during the treatment. This error may particularly result from inaccuracies of the DIR and from deformations of the patient anatomy with respect to the anatomy shown in the analyzed image. Such errors limit the accuracy of the evaluation of a dose distribution with respect to the changed positions and contours of the target structure and the OARs. In particular, this evaluation may include an estimation of the dose absorbed by the target structure and the OARs and the aforementioned error limit the accuracy of this estimate.

Therefore, the planning system includes an evaluation unit 5, which evaluates the relevant dose distribution in view of the contours of anatomic structures and their positions in order to assist in assessing the effects of variations/errors of the contours on the estimated dose delivered to the anatomic structures or on the conformance with dose goals for the anatomic structures.

This evaluation will now be explained with respect to one anatomic structure, which may be the target structure of the radiation therapy treatment or an OAR:

In the evaluation, the evaluation unit 5 evaluates the relevant dose distribution—which may be the dose distribution corresponding to the initial treatment plan or a dose distribution corresponding to an adapted treatment plan—in order to determine whether inaccuracies of the contour of the anatomic structure at one or more points thereof (and in the vicinity of such points) can have a greater influence on the evaluation of the dose delivered to the anatomic structure with respect to the treatment goals. For each relevant position on the contour, the evaluation unit 5 may evaluate the dose distribution at points with varying distances from the relevant position on the contour to determine a point where the dose distribution fulfills a predetermined condition.

The dose distribution may particularly be evaluated along several paths, where each path originates at a certain position on the contour and is configured such that the distance to this position increases when moving along the path starting from the position. In one embodiment, which is referred to herein below by way of example, the paths may be straight rays which are arranged in a certain angle with respect to the contour at the relevant positions of origins of the paths. The angle may particularly be 90° or nearly 90° so that the rays are arranged essentially perpendicular to the contour of the anatomic structure.

The paths or rays may extend either in the inward direction or the outward direction with respect to the anatomic structure. It may also be possible that one path extending in the inward direction and one path extending in the outward direction originate at the same point of the contour of the anatomic structure.

In evaluating the dose distribution along a path, the evaluation unit 5 may determine the first point on the path in the direction of the path (i.e. away from the contour in outward or inward direction), where the evaluated dose distribution fulfills a predetermined condition. The condition and also the direction of the path may be selected on the basis of the type of the anatomic structure (e.g. whether the anatomic structure is the target structure of the radiation therapy treatment or an OAR) and/or on the basis of the dose goal(s) related to the anatomic structure.

Figure 2:
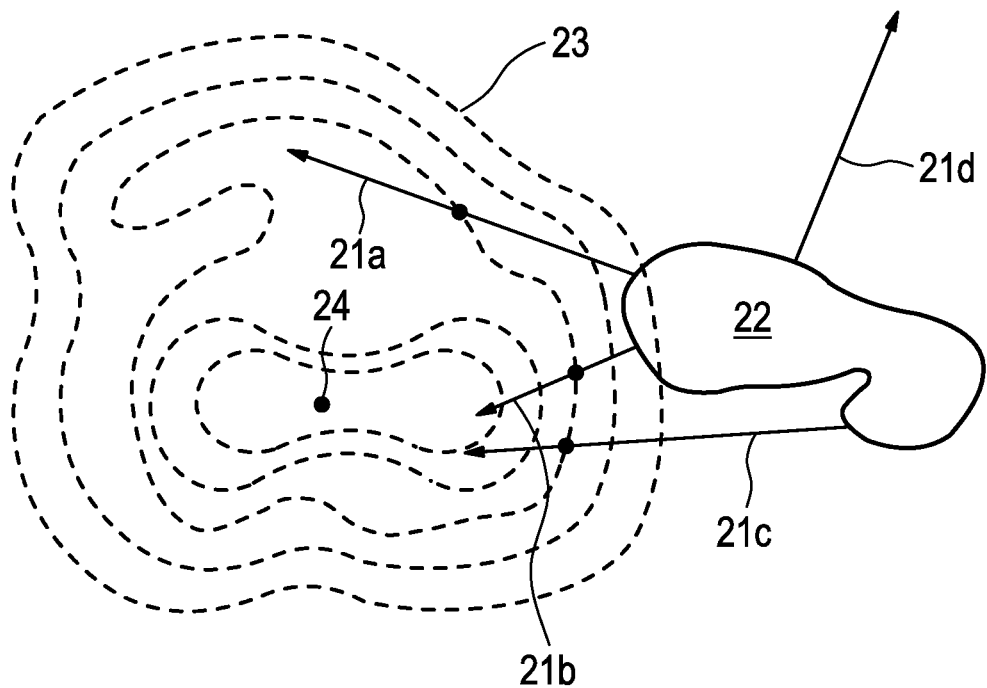

In FIG. 2, several paths 21a-21d, which are configured as straight rays, are illustrated schematically and exemplarily for an OAR 22. In addition, several isodose curves of a dose distribution are shown in dashed lines, where one isodose curve is provided with the reference numeral 23 and where the dose level may decrease with increasing distance from a center point 24. Further, FIG. 2 shows the determined first points on the rays 21a, 21b and 21c, where the dose distribution fulfills a predetermined condition.

In some implementations, the evaluation unit 5 may determine the first point on each path, where the dose distribution has a predetermined characteristic value. The characteristic value may be a dose value included in the dose distribution. In particular, the characteristic value may correspond to a dose value of the dose distribution which corresponds to a particular dose goal for the anatomic structure or which deviates from this dose goal by a predetermined amount.

The paths and their direction may particularly be determined by the evaluation unit 5 on the basis of the dose goals for the anatomic structure and the dose gradient at the contour of the anatomic structure (where the dose values usually decrease in an inward direction in case of an OAR and increase in the inward direction in case of the target structure of the radiation therapy treatment). Moreover, the evaluation unit 5 may define the paths on the basis of the dose values of the points of origin of the paths on the contour of the relevant anatomic structure.

If the dose goal defines an upper limit, as it may be the case for an OAR, the evaluation unit 5 may particularly determine whether the points of origin of envisaged paths on the contour of the anatomic structure comply with the dose goal and whether the dose decreases in the inward direction of the anatomic structure. If so, the evaluation unit 5 may evaluate the dose distribution along paths extending into the outward region of the anatomic structure to determine the first point of each path where the dose value included in the dose distribution corresponds to the dose goal or exceeds the dose goal by a predetermined amount.

For instance, if a maximum allowed dose value or a maximum average dose value is prescribed for the anatomic structure, the evaluation unit 5 may define paths extending into the outward region of the anatomic structure and may determine the first point on each path where the dose value included in the dose distribution corresponds to the maximum allowed dose value or maximum average dose value. As an alternative, the evaluation unit 5 may determine the point on each path where the dose value included in the dose distribution exceeds the maximum allowed dose value or maximum average dose value by a predetermined amount. This amount may be specified by means of an absolute margin or a percentage of the maximum allowed dose value or the maximum average dose value. This alternative may particularly be applied in case the characteristic value corresponds to an average dose value, since local deviations from such an average value do not prevent the dose goal from being achieved.

In one embodiment, the evaluation unit 5 may also define paths if the dose values at their origins do not comply with the upper limit specified by the dose goal and evaluate the dose distribution along these paths. For instance, if the dose value on a contour of an OAR, for which a maximum dose is specified, is larger than the maximum dose, the evaluation unit 5 may define a path directed to the inside of the OAR and determine the first point on the path, where the dose value according to the dose distribution corresponds to the maximum value.

If the dose goal defines a lower limit, as it may be the case for the target structure of the radiation therapy treatment, the evaluation unit 5 may determine whether the points of origin of envisaged paths on the contour of the anatomic structure comply with the dose goal and whether the dose increases in the inward direction of the anatomic structure. If so, the evaluation unit 5 may evaluate the dose distribution along paths extending into the inward region of the anatomic structure to determine the first point of each path where the dose value included in the dose distribution corresponds to the dose goal or where the dose value is lower than the dose goal by a predetermined amount.

If a minimum dose value or a minimum average dose value is prescribed for the anatomic structure, the evaluation unit 5 may define paths extending into the inward region of the anatomic structure and may determine the first point on each path where the dose value included in the dose distribution corresponds to the minimum dose value or minimum average dose value. As an alternative, the evaluation unit 5 may determine the first point on each path where the dose value included in the dose distribution is lower than the minimum dose value or minimum average dose value by a predetermined amount which may again be specified by means of an absolute margin or a percentage of the minimum dose value or the minimum average dose value. Again, this alternative may particularly be applied in case of an average dose value.

Moreover, the evaluation unit 5 may also define paths if the dose values at their origins do not comply with the lower limit specified by the dose goal and evaluate the dose distribution along these paths. For instance, if the dose value of a contour of target structure, for which a minimum dose is specified, is smaller than the minimum dose, the evaluation unit 5 may define a path directed to the outside of the target structure and determine the first point on the path, where the dose value according to the dose distribution corresponds to the minimum value.

In order to increase the robustness of the evaluation of the contour in case of large dose variations (i.e. high dose gradients) in the dose distribution, the evaluation unit 5 may determine the first point on each path which has a neighborhood of predetermined size that includes a dose value corresponding to the characteristic dose value as explained above. Thus, not only the dose value at each point along the path is compared with the relevant characteristic dose goal value, but for each position on the path the dose values in a region surrounding the position are also compared with the characteristic value in the way described above. Hereby, it is ensured that dose values of the dose distribution are taken into consideration, which correspond to the relevant characteristic value (e.g. a minimum or maximum dose value) and which do not occur on one of the paths but at positions in the vicinity of one or more paths.

In a further embodiment, the evaluation unit 5 may evaluate the cumulative dose along a path, i.e. the sum of doses delivered to the points on the path, and may determine the point on the path, where the cumulated dose exceeds a predetermined threshold. This embodiment may particularly be applied in case of a small OAR for which a maximum overall dose is specified as a treatment goal. For such an OAR, the point where the cumulated dose along the path exceeds a threshold provides an indication how far the contour of the OAR could be shifted into a higher dose region of the dose distribution without violating the treatment goal. The threshold may be determined on the basis of the difference between the maximum overall dose specified for the OAR and the overall dose delivered to the OAR in accordance with the evaluated dose distribution on the basis of the transformed contour.

In order to evaluate the transformed contour of the anatomic structure, the evaluation unit 5 may evaluate the dose distribution along a plurality of paths extending from the contour. In one embodiment, the contour may be divided into surface elements in accordance with a particular pattern and the evaluation unit 5 may evaluate the dose distribution along one path for each surface element. In one embodiment, the surface elements may be constructed in the evaluation unit 5 in order to arrange the paths on the contour of the anatomic structure. In a further embodiment, the contour may be formed from a plurality of surface elements in the segmentation procedure and the evaluation unit 5 may evaluate one path for each of these surface elements.

In view of the assessment of the accuracy of the contour of the anatomic structure with respect to the evaluation of the dose distribution, the distances between the contour and the points determined on the paths as explained above are of particular interest. If one or more of these distances are small, the inaccuracies of the contour of the anatomic structure may prevent a proper evaluation of the dose distribution with respect to the contour. Therefore, positions on the surface and or surface elements may be identified, where rays originate on which points have been determined that have a small distance to the contour. This may be done automatically and or manually by the user of the system.

In order to allow for a manual identification of such positions or surface elements, the evaluation unit 5 may visualize the paths and/or the determined points on the paths at the display unit 2. In particular, the paths and/or the determined points of the paths may be displayed together with the relevant (transformed) contour of the anatomic structure. Moreover, the paths and/or the determined points and the contour of the anatomic structure may be overlaid over the image on the basis of which the contour has been determined. In addition, also the dose distribution to be evaluated may be overlaid over the respective image. In order to visualize the paths and the points determined on the paths, arrows may particularly be displayed which extend along the rays to the points determined thereon. However, other visualizations are likewise possible.

In a variant of this embodiment, the evaluation unit 5 may generate a sensitivity region which includes a region between the contour of the anatomic structure and a surface including the points determined on the paths, which may be constructed from these points in a suitable way. In this embodiment, the paths may be configured as straight rays arranged essentially perpendicular to the contour as explained above. The sensitivity region may then be displayed together with the contour of the anatomic structure, e.g. be coloring the sensitivity region using a predetermined color. As explained above, this visualization may also be overlaid over the image of the region of interest of the patient body, optionally together with the dose distribution to be evaluated.

In the visualizations according to the aforementioned embodiments, the evaluation unit 5 may also distinguish between paths originating at positions on the contour which fulfill the relevant dose goal and/or determined points on such paths and paths originating at positions on the contour which do not fulfill the relevant dose goal. This may be made using different colors.

On the basis of a visualization of the aforementioned kind, the user of the planning system may identify positions on the contour of the anatomic or sections thereof, where paths originate on which points have been determined that have a small distance to the contour.

In addition or as an alternative, such positions or sections may be determined automatically by means of the evaluation unit 5. For this purpose, the evaluation unit 5 may determine the distances between the points determined on the paths and the contour and may compare these distances with a predetermined threshold value. In view of the inaccuracies resulting from the DIR, the threshold may be in the range of the inaccuracy of the DIR algorithm used for determined the transformed contour of the anatomic structure. In view of inaccuracies due to deformations of the patient anatomy, the threshold may be determined on the basis of an expected amount of such deformation. In one embodiment, it is also possible to compare the distances with both thresholds.

If at least one distance is smaller than the relevant threshold value, the evaluation unit 5 may automatically reject the contour of the anatomic structure and initiate a new delineation of the anatomic contour.

As an alternative, the evaluation unit 5 may visualize the result of the comparison with the threshold to the user of the system. If the distance is smaller than the threshold for one or more paths, the root points of these rays or the surface elements including the root points may be marked as critical. The corresponding paths and/or their foot points may also be highlighted in a visualization of the contour of the anatomic structure, which may additionally include a visualization of the rays and/or the points determined on the rays as explained above or which may not include such visualization. Also in the latter case, the visualization of the contour of the anatomic structure may be overlaid over the image of the region of interest of the patient body and over the dose distribution to be evaluated. The highlighting may be achieved by coloring the critical positions and/or surface elements using a predetermined color, for example.

Moreover, the evaluation unit 5 may again distinguish between foot points of paths, which fulfill the relevant dose goal, and food points of paths, which do not fulfill the relevant dose goal. This may be made using different colors. In a variant of the aforementioned embodiment, the evaluation unit 5 may provide the points of origin of the paths on the contour with several colors in accordance with the distances between these points of origin and the points determined on the rays. For this purpose, the range of possible distances may be divided into a number of intervals and each interval may be associated with a color. A point of origin of a path may then be provided with the color associated with the interval in which the distance between this point and the point on the path originating at this point is included. Preferably, the number of colors or intervals is greater than three or four. Thus, the user of the planning system can determine the distance between the points on the contour and the points determined on the related paths on the basis of the intervals in more detail than in the above-mentioned embodiment, in which the visualization only distinguishes between critical and non-critical points.

If critical points on the contour of the anatomical structure or critical surface elements are manually or automatically identified as explained above and the contour of the anatomic structure has been determined using DIR, the contour may be compared with the actual delineation of the anatomic structure as shown in the image and may be corrected to precisely correspond to this delineation, if necessary. This may again be made by means of a manual, semi-automatic or automatic delineation procedure. On the basis of the corrected contour, the dose distribution may then be evaluated with respect to the contour, e.g. in order to assess whether predetermined dose goals for the anatomic structure can be fulfilled. In this assessment, inaccuracies of the contour due to deformations of the patient anatomy may again be considered as described above.

In another variant, the evaluation unit 5 may also determine a position on the contour of the anatomic structure, where errors of the contour have the highest influence on the conformance with a dose goal. This position may correspond to the origin of a path on which a point has been determined as described above, which has the closest distance to the contour among all determined points. The relevant position may be highlighted in a visualization of the contour in addition or as an alternative to the displaying of the information mentioned above.

On the basis of this highlighting, the user of the system can directly assess and review the most sensitive position on the contour and evaluate the dose distribution particularly with respect to the part of the contour at this position. This allows for a more efficient evaluation of dose distribution with respect to the contour. For instance, the user may newly delineate the contour at this position. If the user then determines that the treatment goals will likely not be met on the basis of the new delineation, the user may initiate a re-planning without a review of further (less sensitive) sections of the contour.

In the aforementioned embodiments of the planning system, the determined contour of an anatomic structure can be evaluated in view of its accuracy with respect to the assessment of a dose distribution. Moreover, the contour can be further validated and corrected, if necessary, in case its accuracy is not sufficient for assessing the dose distribution. In this respect, a reliable assessment of the dose distribution on the basis of the transformed contour is possible without having to newly segment and delineate the complete anatomic structure.

Figure 3:
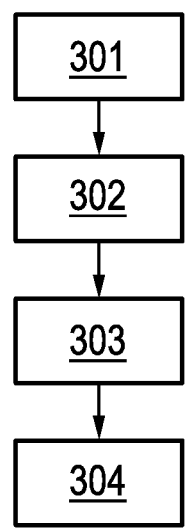

FIG. 3 schematically and exemplarily illustrates steps carried out in the evaluation unit 5 of the planning system in order to evaluate the contour of an anatomic structure in view of its accuracy with respect to the assessment of a dose distribution. In step 301, the evaluation unit 5 receives the contour of the anatomic structure and the dose distribution. The dose distribution corresponds to a treatment plan. As said above, this may be an initial treatment plan or an already adapted treatment plan for a patient. In step 302, the evaluation unit 5 then evaluates the dose distribution in varying distances from the contour of the anatomic structure to determine at least one point where the evaluated dose distribution fulfills a predetermined condition. Exemplary conditions have been described above. In order to determine the at least one point, the evaluation unit 5 may evaluate the dose distribution along one or more paths extending from the contour of the anatomic structure. In step 303, the evaluation unit 5 may determine the distance between the at least one point and the contour in order to provide a visualization on the basis of the distance as described above. In addition or as an alternative, evaluation unit may visualize the at least one point in step 304, e.g. when visualizing a sensitivity region as explained above.

Variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality.

A single unit or device may fulfill the functions of several items recited in the claims. The mere fact that certain measures are recited in mutually different dependent claims does not indicate that a combination of these measures cannot be used to advantage.

A computer program may be stored/distributed on a suitable medium, such as an optical storage medium or a solid-state medium, supplied together with or as part of other hardware, but may also be distributed in other forms, such as via the Internet or other wired or wireless telecommunication systems.

Any reference signs in the claims should not be construed as limiting the scope.

The invention claimed is:

1. System for assisting in evaluating a contour of an anatomic structure with respect to a dose distribution corresponding to a treatment plan for a radiation therapy treatment of a patient, the system comprising an evaluation unit configured to
receive the contour of the anatomic structure and the dose distribution,
evaluate the dose distribution in varying distances from the contour of the anatomic structure to determine at least one point where the evaluated dose distribution fulfills a predetermined condition, and
determine the distance between the at least one point and the contour and/or to visualize the at least one point to a user of the system.

2. The system as defined in claim 1, wherein the evaluation unit is configured to determines the at least one point by evaluating the dose distribution along at least one path extending from the contour of the anatomic structure in an inward or outward direction, the at least on point lying on the at least one path.

3. The system as defined in claim 2, wherein the path corresponds to a ray being arranged essentially perpendicular to the contour of the anatomic structure.

4. The system as defined in claim 1, wherein the predetermined condition and/or the direction of the path is selected on the basis of a type of the anatomic structure and/or on the basis of the dose goal to be achieved for the anatomic structure in the radiation therapy treatment.

5. The system as defined in claim 1, wherein the predetermined condition is fulfilled if the dose distribution has a predetermined characteristic value.

6. The system as defined in claim 1, wherein the characteristic value corresponds to a predetermined maximum dose value or a predetermined minimum dose value.

7. The system as defined in claim 6, wherein the maximum dose value corresponds to a maximum dose or a maximum average dose to be delivered to the anatomic structure during the treatment or to a dose value exceeding the maximum dose or the maximum average dose by a predetermined amount.

8. The system as defined in claim 6, wherein the minimum dose value corresponds to a minimum dose or a minimum average dose to be delivered to the anatomic structure during the treatment or to a dose value lower than the minimum dose or the minimum average dose by a predetermined amount.

9. The system as defined in claim 1, wherein the predetermined condition is fulfilled if the dose distribution has a predetermined characteristic value in a region surrounding the at least one point.

10. The system as defined in claim 1, wherein the predetermined condition relates to dose goal to be achieved for the anatomic structure in the radiation therapy treatment and wherein the evaluation unit is configured visualize information indicative of the influence of an error of at least part of the contour on a conformance with the dose goal as determined on the basis of the dose distribution and the contour, the information being derived from the at least one point and/or from the determined distance between the at least one point and the contour.

11. The system as defined in claim 1, wherein the evaluation unit is configured to determine plural points where the evaluated dose distribution fulfills the predetermined condition and to display a sensitivity region, which is bounded by the contour of the anatomic structure and the plural points, to the user of the system.

12. The system as defined in claim 1, wherein the evaluation unit is further configured to compare the distance between the at least one point and the contour of the anatomic structure with a predetermined threshold.

13. The system as defined in claim 1, wherein the evaluation unit is configured to display a visualization highlighting an origin of the path on the contour of the anatomic structure, if the distance between the at least one point on the at least one path and the contour of the anatomic structure is smaller than the predetermined threshold.

14. A method for assisting in evaluating a contour of an anatomic structure with respect to a dose distribution corresponding to a treatment plan for a radiation therapy treatment of a patient, the method comprising:
receiving the contour of the anatomic structure and the dose distribution,
evaluating the dose distribution in varying distances from the contour of the anatomic structure to determine at least one point where the evaluated dose distribution fulfills a predetermined condition, and
determining the distance between the at least one point and the contour and/or visualizing the at least one point to a user of the system.

15. A computer program comprising program code for instructing a computer device to perform a method as defined in claim 14 when the program code is executed in the computer device.

* * * * *